(12) United States Patent
Mikami

(10) Patent No.: US 10,912,448 B2
(45) Date of Patent: Feb. 9, 2021

(54) CABLE CONNECTION STRUCTURE, IMAGING MODULE, AND ENDOSCOPE

(71) Applicant: OLYMPUS CORPORATION, Tokyo (JP)

(72) Inventor: Masato Mikami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 372 days.

(21) Appl. No.: 15/968,824

(22) Filed: May 2, 2018

(65) Prior Publication Data
US 2018/0249896 A1 Sep. 6, 2018

Related U.S. Application Data

(63) Continuation of application No. PCT/JP2015/081452, filed on Nov. 9, 2015.

(51) Int. Cl.
*A61B 1/00* (2006.01)
*A61B 1/05* (2006.01)
(Continued)

(52) U.S. Cl.
CPC ...... *A61B 1/00124* (2013.01); *A61B 1/00018* (2013.01); *A61B 1/00114* (2013.01);
(Continued)

(58) Field of Classification Search
CPC .. A61B 1/00124; H01B 11/002; H01B 11/20; H01R 4/024
See application file for complete search history.

(56) References Cited

U.S. PATENT DOCUMENTS 4,831,456 A * 5/1989 Takamura ............... A61B 1/05
348/294
10,281,711 B2 * 5/2019 Kitano ............... A61B 1/00096
(Continued)

FOREIGN PATENT DOCUMENTS

JP 2000-125161 A 4/2000
JP 2008-192358 A 8/2008
(Continued)

OTHER PUBLICATIONS

International Search Report dated Jan. 26, 2016 issued in PCT/JP2015/081452.

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

A cable connection structure includes: a substrate including a first core wire connection electrode, a second core wire connection electrode, and a shield connection electrode; a single-wire cable including a first core wire, and an insulant; at least two coaxial cables each including a second core wire, an inner insulant, a shield, and an outer insulant, wherein the second core wire, the inner insulant, and the shield are exposed in a step-by-step manner at a distal end portion, and the second core wire and the shield are respectively connected to the second core wire connection electrode and the shield connection electrode; and a conductive member connecting exposed portions of the shields. The conductive member is disposed directly on an upper surface of the insulant, and connects the shields on the shield connection electrode and/or a position closer to a proximal end side than the shield connection electrode.

8 Claims, 12 Drawing Sheets

(51) Int. Cl.
*A61B 1/04* (2006.01)
*H01R 4/02* (2006.01)
*H01R 12/62* (2011.01)
*H01B 11/00* (2006.01)
*H01B 11/18* (2006.01)
*H01B 11/20* (2006.01)

(52) U.S. Cl.
CPC ................ *A61B 1/04* (2013.01); *A61B 1/051* (2013.01); *H01B 11/002* (2013.01); *H01B 11/1895* (2013.01); *H01B 11/20* (2013.01); *H01R 4/024* (2013.01); *H01R 4/027* (2013.01); *H01R 12/62* (2013.01)

(56) References Cited

U.S. PATENT DOCUMENTS

| | | |
|---|---|---|
| 2010/0231702 A1 | 9/2010 | Tsujimura et al. |
| 2013/0005181 A1 | 1/2013 | Yamada et al. |
| 2013/0008694 A1* | 1/2013 | Takamatsu ......... A61B 1/00018 174/250 |
| 2014/0220822 A1* | 8/2014 | Keyser ............... H01R 13/6592 439/607.46 |

FOREIGN PATENT DOCUMENTS

| | | |
|---|---|---|
| JP | 2009-082504 A | 4/2009 |
| JP | 2010-068930 A | 4/2010 |
| JP | 2011-222277 A | 11/2011 |
| WO | WO 2009/139041 A1 | 11/2009 |

* cited by examiner

CABLE CONNECTION STRUCTURE, IMAGING MODULE, AND ENDOSCOPE

CROSS-REFERENCE TO RELATED APPLICATION

This application is a continuation of International Application No. PCT/JP2015/081452, filed on Nov. 9, 2015, the entire contents of which are incorporated herein by reference.

BACKGROUND

The present disclosure relates to a cable connection structure, an imaging module, and an endoscope.

Endoscopes are widely used for various inspections in the medical field and the industrial field. Among these endoscopic devices, a medical endoscopic device may acquire an in-vivo image of the inside of a subject without cutting open the subject, by inserting, into the subject such as a patient, a flexible insertion portion having an elongated shape and having a solid state image sensor provided at a distal end, and may further perform remedial treatment while causing, as necessary, a processing tool to protrude from an insertion portion distal end. Thus, such a medical endoscopic device is widely used.

In a distal end portion of the insertion portion of such an endoscope, an imaging module including a solid state image sensor, and a circuit substrate to which a coaxial cable is connected is incorporated, and a curve portion that may be freely curved in a plurality of directions is connected to a proximal end side of the distal end portion. Because the curve portion is curved in four directions in a subject, stress in a radial direction is added also to the content of the insertion portion according to the bending of the curve portion. For preventing cable disconnection and detachment or the like of a soldered portion that are caused by the stress, there is proposed an imaging apparatus in which, in connecting a core wire and a shield of a coaxial cable to a substrate, the core wire that is easily detached by the load of stress is connected to the substrate in a looser state than the shield (e.g., refer to JP 2010-68930 A).

SUMMARY

A cable connection structure includes: a substrate including a first core wire connection electrode, a second core wire connection electrode, and a shield connection electrode; a single-wire cable including a first core wire made of electrically-conductive material, and an insulant covering an outer periphery of the first core wire, wherein the first core wire is exposed at a distal end portion, and connected to the first core wire connection electrode; at least two coaxial cables each including a second core wire made of electrically-conductive material, an inner insulant covering an outer periphery of the second core wire, a shield made of electrically-conductive material that covers an outer periphery of the inner insulant, and an outer insulant covering an outer periphery of the shield, wherein the second core wire, the inner insulant, and the shield are exposed in a step-by-step manner at a distal end portion, and the second core wire and the shield are respectively connected to the second core wire connection electrode and the shield connection electrode; and a conductive member connecting exposed portions of the shields of the two coaxial cables, wherein the single-wire cable is disposed between the two coaxial cables, the conductive member is disposed directly on an upper surface of the insulant covering the single-wire cable, and the conductive member connects the shields on at least one of a position on the shield connection electrode and a position closer to a proximal end side than the position on the shield connection electrode.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
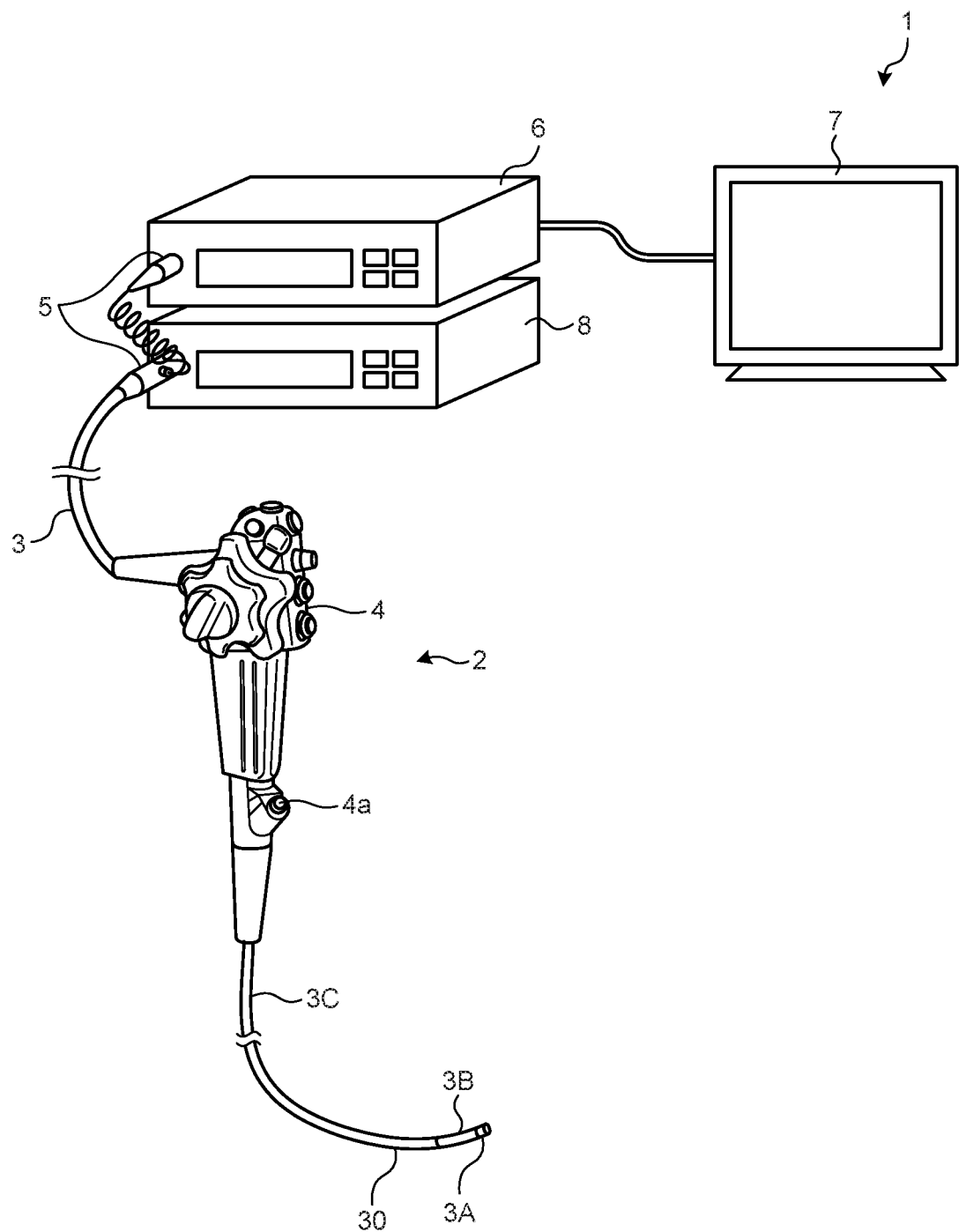
FIG. 1 is a diagram schematically illustrating an entire configuration of an endoscope system according to a first embodiment.

In the following description, as a mode for carrying out the present disclosure (hereinafter, referred to as an "embodiment"), an endoscope system including an imaging module will be described. In addition, this disclosure is not limited by this embodiment. Furthermore, in the description of the drawings, the same parts are assigned the same signs. Furthermore, it should also be noted that the drawings are schematic drawings, and relationship between thickness and width of each member, proportion of each member, and the like differ from reality. In addition, also in the drawings, parts having dimensions and proportions that are different from each other are included.

First Embodiment

FIG. 1 is a diagram schematically illustrating an entire configuration of an endoscope system according to an embodiment. As illustrated in FIG. 1, an endoscope system 1 includes an endoscope 2, a universal cord 3, a connector portion 5, a processor (control device) 6, a display device 7, and a light source device 8.

The endoscope 2 inserts an insertion portion 30 into a subject, thereby capturing an in-vivo image of the subject, and outputting an imaging signal. An electrical cable bundle provided inside the universal cord 3 is extended to the insertion portion 30 of the endoscope 2, and connects to an imaging apparatus provided at a distal end portion 3A of the insertion portion 30.

An operating unit 4 provided with various buttons and knobs for operating an endoscopic function is connected to a proximal end side of the insertion portion 30 of the endoscope 2. The operating unit 4 is provided with a processing tool insertion port 4a through which a processing tool such as biological forceps, an electrical cautery, and an inspection probe is inserted into a body cavity of the subject.

The connector portion 5 is provided at a proximal end of the universal cord 3, is connected to the light source device 8 and the processor 6, performs predetermined signal processing on the imaging signal output by the imaging apparatus provided at the distal end portion 3A connecting with the universal cord 3, and performs analog-digital conversion (A/D conversion) of the imaging signal, to output the converted signal as an image signal.

The processor 6 performs predetermined image processing on the image signal output from the connector portion 5, and controls the entire endoscope system 1. The display device 7 displays an image signal on which the processor 6 has performed processing.

Pulsed white light lit by the light source device 8 passes through the universal cord 3 and the connector portion 5, to become illumination light to be emitted from the distal end of the insertion portion 30 of the endoscope 2 toward the subject. The light source device 8 is formed by using a white LED, for example.

The insertion portion 30 includes the distal end portion 3A provided with an imaging module, a curve portion 3B provided next to the proximal end side of the distal end portion 3A that may be freely curved in a plurality of directions, and a flexible tube portion 3C provided next to the proximal end side of the curve portion 3B. An imaging signal of an image captured by the imaging module provided at the distal end portion 3A is connected to the connector portion 5 via the operating unit 4 by the universal cord 3 having a length of several meters, for example. The curve portion 3B is curved by an operation of a curve operation knob provided in the operating unit 4, and may be freely curved in four directions of up, down, left, and right, for example, in accordance with pulling or loosening of a curve wire inserted into the insertion portion 30.

In the endoscope 2, a light guide handle (not illustrated) for transmitting illumination light from the light source device 8 is provided, and an illumination lens (not illustrated) is disposed at an exit end of the illumination light caused by the light guide handle. The illumination lens is provided at the distal end portion 3A of the insertion portion 30, and the illumination light is emitted toward the subject.

Figure 2:
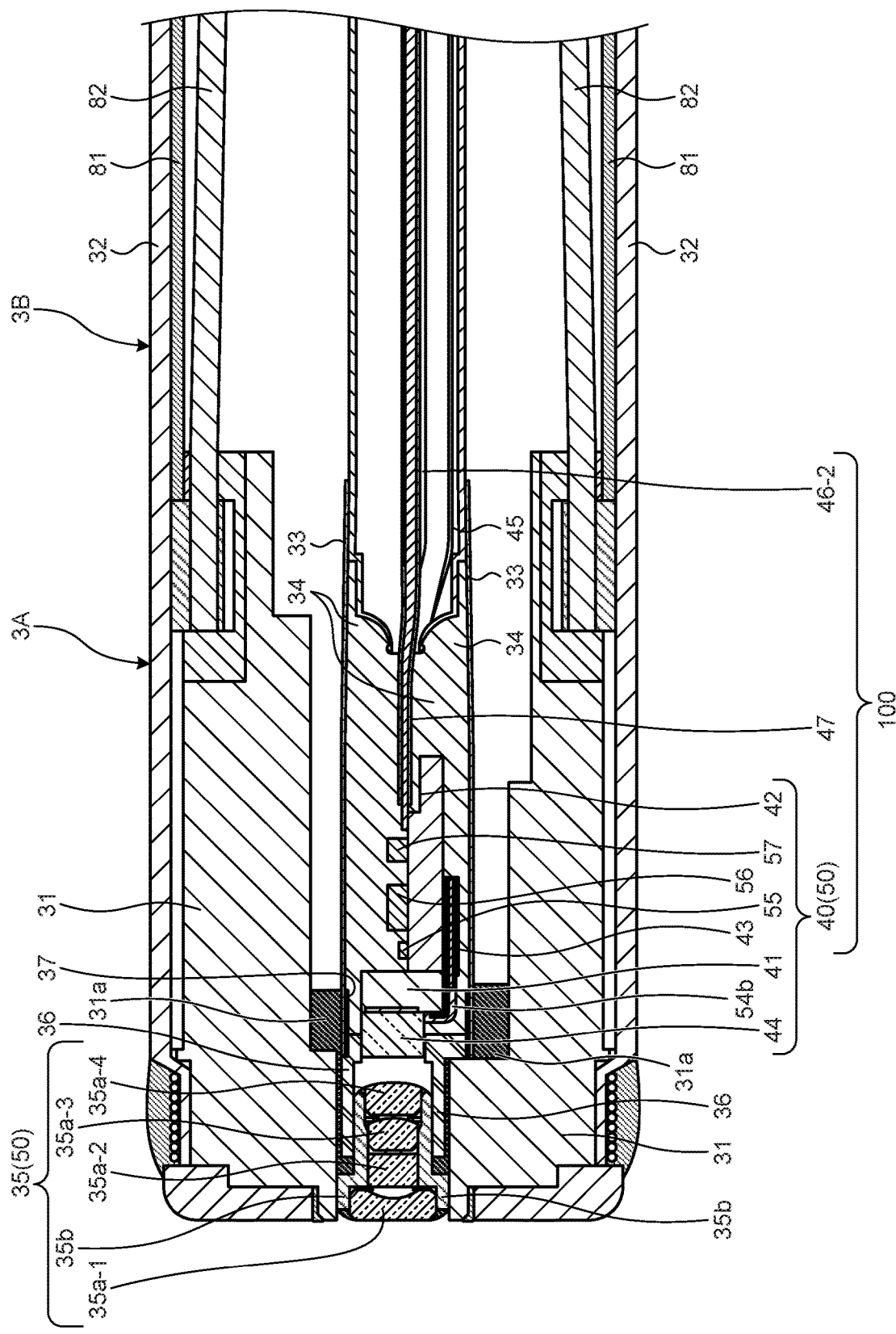
FIG. 2 is a partial cross-sectional view of an endoscope distal end illustrated in FIG. 1.

Next, a configuration of the distal end portion 3A of the endoscope 2 will be described. FIG. 2 is a partial cross-sectional view of the distal end of the endoscope 2. FIG. 2 is a cross-sectional view obtained by cutting along a plane that is perpendicular to a substrate plane of the imaging module provided at the distal end portion 3A of the endoscope 2, and is parallel to a light axis direction of the imaging module. In FIG. 2, the distal end portion 3A of the insertion portion 30 of the endoscope 2, and part of the curve portion 3B are illustrated.

As illustrated in FIG. 2, the curve portion 3B may be freely curved in four directions of up, down, left, and right in accordance with pulling or loosening of a curve wire 82 inserted into a curve tube 81 disposed inside a cladding tube 32 to be mentioned later. An imaging module 100 is provided in the distal end portion 3A extended to the distal end side of the curve portion 3B.

The imaging module 100 includes an imaging apparatus 50 including a lens unit 35 and an imaging unit 40, and a signal cable 45. The imaging unit 40 is disposed on the proximal end side of the lens unit 35, and is adhered to the inside of a distal end portion main body 31 by adhesive 31a. The distal end portion main body 31 is formed of a rigid member for forming an internal space for accommodating the imaging module 100. A proximal end outer peripheral portion of the distal end portion main body 31 is covered by the flexible cladding tube 32. A member provided on the proximal end side of the distal end portion main body 31 is formed of a flexible member so that the curve portion 3B may be curved. The distal end portion 3A at which the distal end portion main body 31 is provided corresponds to a rigid portion of the insertion portion 30.

The lens unit 35 includes a plurality of objective lenses 35a-1 to 35a-4, and a lens holder 35b for holding the objective lenses 35a-1 to 35a-4, and the distal end of the lens holder 35b is fixed to the distal end portion main body 31 by being inserted into the distal end portion main body 31.

The imaging unit 40 includes a solid state image sensor 41 including a light receiving unit that generates an electrical signal by receiving light of a charge-coupled device (CCD), a complementary metal-oxide semiconductor (CMOS), or the like, and performing photoelectric conversion, a circuit substrate 42 connected to a back surface of the solid state image sensor 41, a flexible printed substrate 43 (hereinafter, referred to as an "FPC substrate 43") extending from a rear surface side of a light receiving surface of the solid state image sensor 41 in the light axis direction, a glass lid 44 to be adhered to the solid state image sensor 41 in a state of covering the light receiving surface of the solid state image sensor 41, and the signal cable 45 to be connected to the circuit substrate 42. On the circuit substrate 42 of the imaging unit 40, electronic components 55 to 57 forming a drive circuit of the solid state image sensor 41 are mounted. Electronic components other than the electronic components forming the drive circuit of a solid state image sensor 41 may be mounted on the circuit substrate 42.

The proximal end of the signal cable 45 extends in a proximal end direction of the insertion portion 30. The signal cable 45 is inserted into and disposed in the insertion portion 30, and is extended to the connector portion 5 via the operating unit 4 and the universal cord 3 illustrated in FIG.

1. In this first embodiment, the signal cable 45 includes two coaxial cables 46-1 and 46-2 (refer to FIG. 3), and one single-wire cable 47.

A subject image formed by the objective lenses 35a-1 to 35a-4 of the lens unit 35 is detected by the solid state image sensor 41 provided at an image forming position of the objective lenses 35a-1 to 35a-4, and is converted into an imaging signal. The imaging signal passes through the signal cable 45 connecting to the FPC substrate 43 and the circuit substrate 42, and the connector portion 5, to be output to the processor 6.

The solid state image sensor 41 is adhered to the FPC substrate 43 and the circuit substrate 42. Connection portions provided between the solid state image sensor 41, and the solid state image sensor 41 and the FPC substrate 43 are covered by a metal reinforcement member 37. For preventing influence of external static electricity on the electronic components 55 to 57 on the circuit substrate 42, the reinforcement member 37 is installed at a distance from the solid state image sensor 41, the FPC substrate 43, and the circuit substrate 42.

The outer periphery of the imaging apparatus 50 is covered by a heat shrinkable tube 33 for enhancing resistance properties. In the heat shrinkable tube 33, clearance gaps between components are filled by adhesive resin 34.

A solid state image sensor holder 36 holds the solid state image sensor 41 adhered to the glass lid 44, by fitting an outer peripheral surface of the glass lid 44 into a proximal end side inner peripheral surface of the solid state image sensor holder 36. The proximal end side outer peripheral surface of the solid state image sensor holder 36 fits with a distal end side inner peripheral surface of the reinforcement member 37. A proximal end side outer peripheral surface of the lens holder 35b fits with a distal end side inner peripheral surface of the solid state image sensor holder 36. In a state in which the members are fitted with each other in this manner, the outer peripheral surface of the lens holder 35b, the outer peripheral surface of the solid state image sensor holder 36, and a distal end side outer peripheral surface of the heat shrinkable tube 33 are fixed to a distal end inner peripheral surface of the distal end portion main body 31 by the adhesive 31a.

Figure 3:
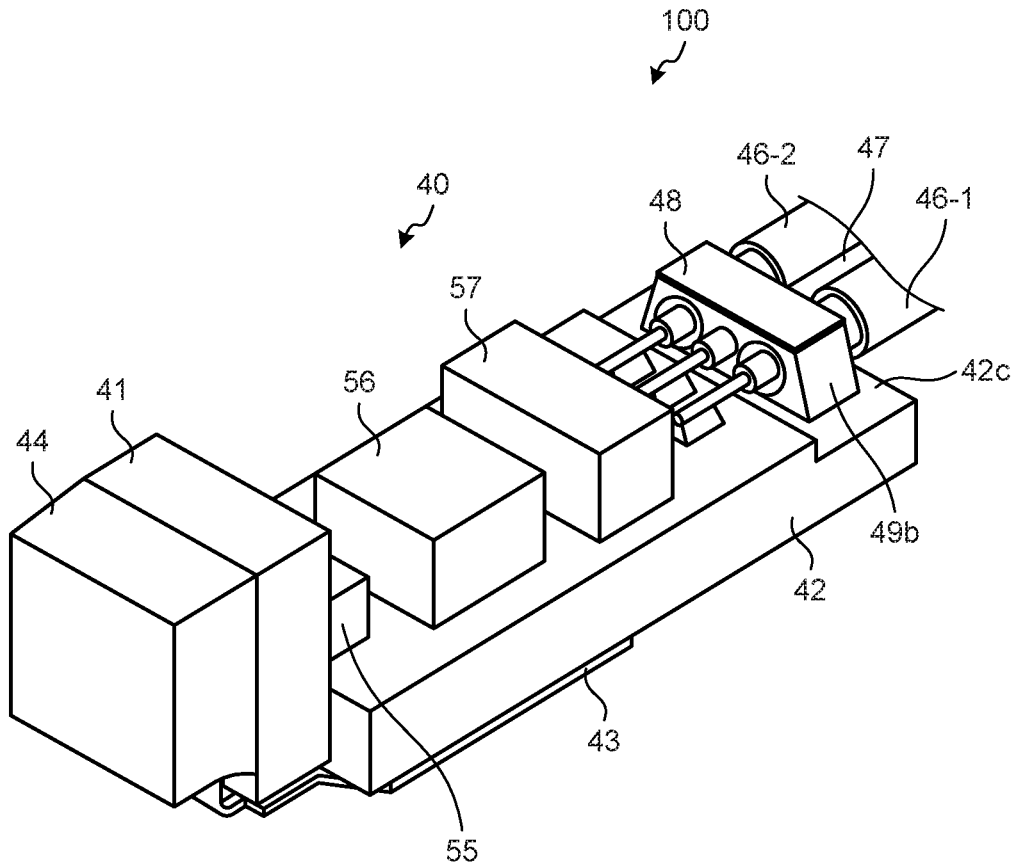
FIG. 3 is a perspective view of an imaging module illustrated in FIG. 2.
Figure 4:
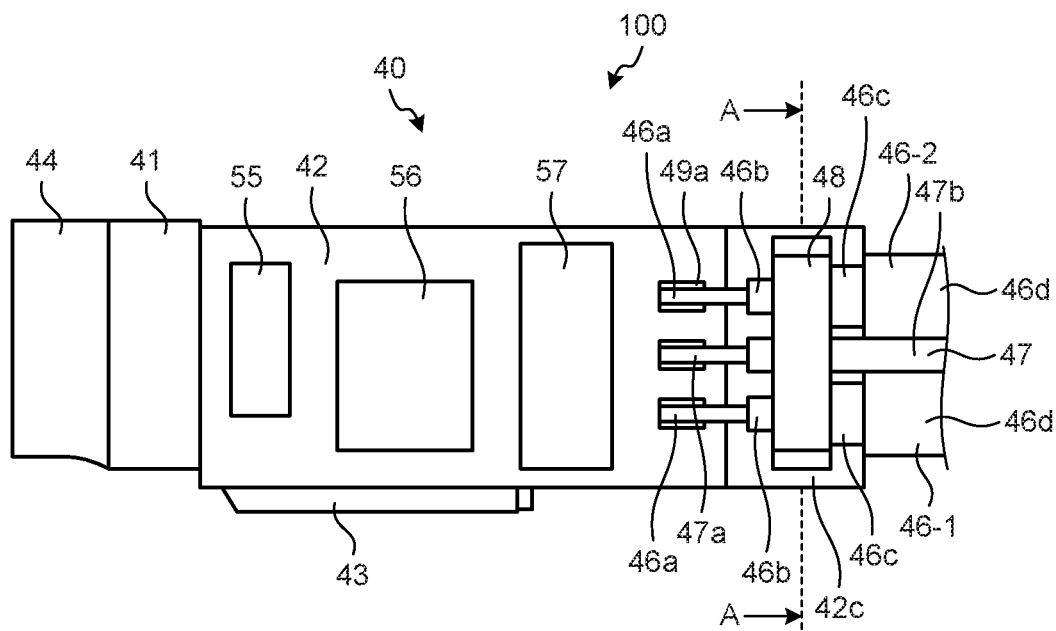
FIG. 4 is a top view of the imaging module illustrated in FIG. 3.
Figure 5:
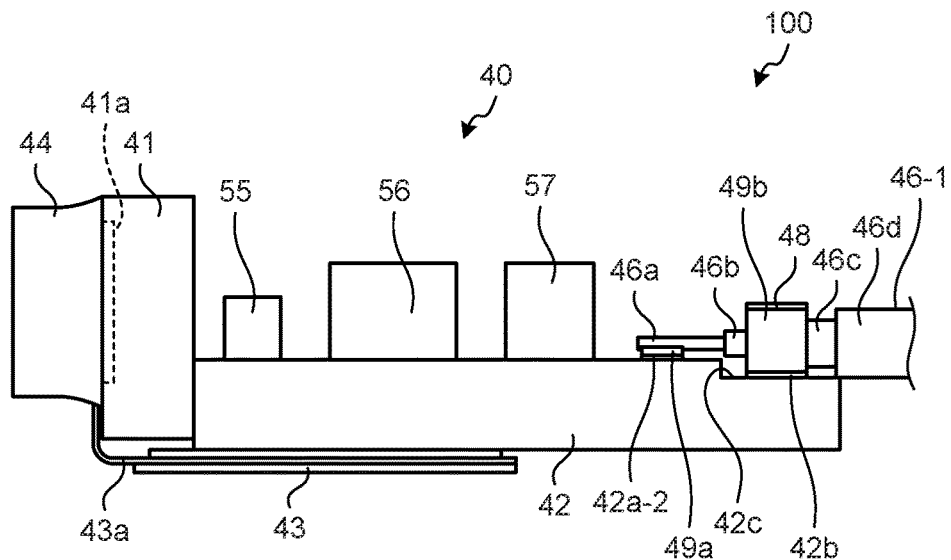
FIG. 5 is a side view of the imaging module illustrated in FIG. 3.
Figure 6:
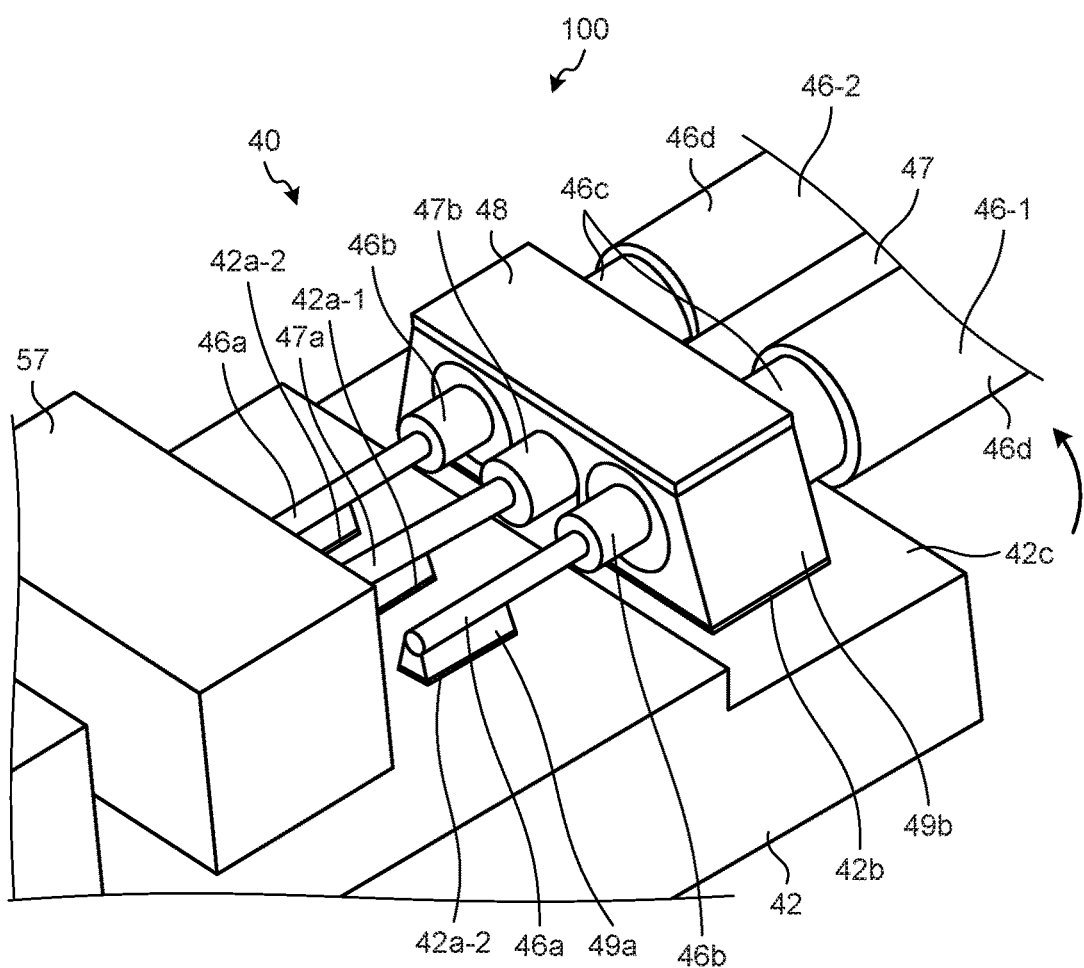
FIG. 6 is a partially-enlarged perspective view of the imaging module illustrated in FIG. 3.
Figure 7:
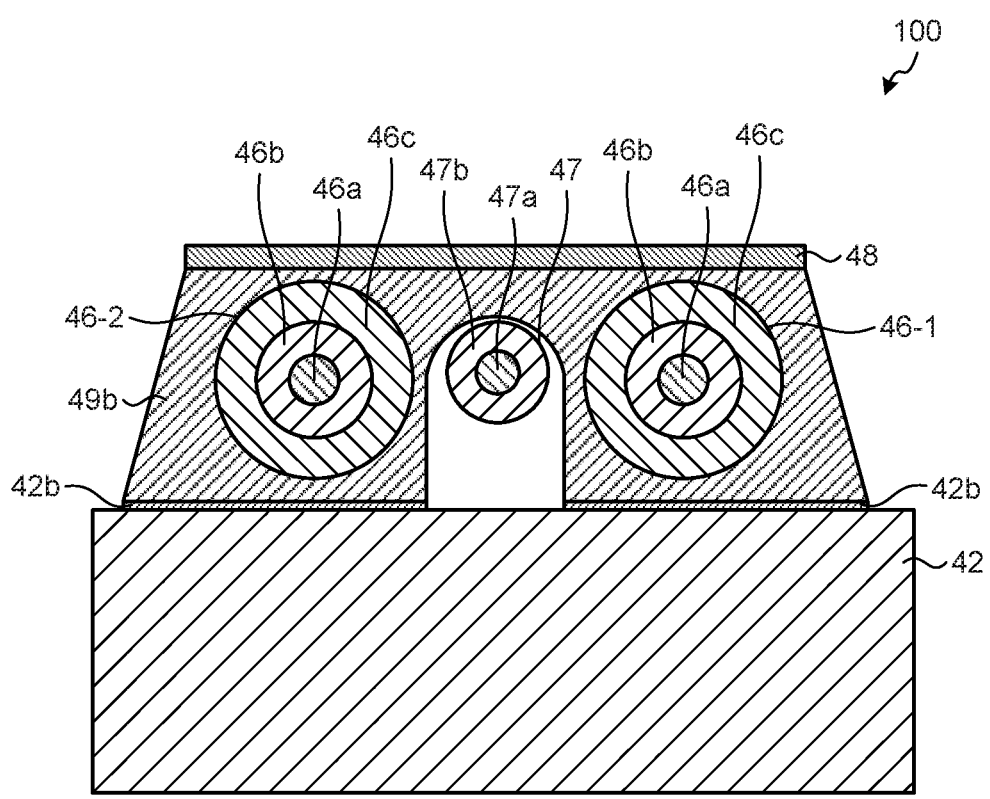
FIG. 7 is an A-A line cross-sectional view of the imaging module illustrated in FIG. 4.

Next, the imaging module 100 will be described in detail. FIG. 3 is a perspective view of the imaging module illustrated in FIG. 2. FIG. 4 is a top view of the imaging module illustrated in FIG. 3. FIG. 5 is a side view of the imaging module illustrated in FIG. 3. FIG. 6 is a partially-enlarged perspective view of the imaging module illustrated in FIG. 3. FIG. 7 is an A-A line cross-sectional view of the imaging module illustrated in FIG. 4. In addition, in FIGS. 3 to 7, the illustration of the lens unit 35 is omitted. The imaging module 100 according to the first embodiment includes the imaging apparatus 50 including the lens unit 35 and the imaging unit 40, the two coaxial cables 46-1 and 46-2, and the one single-wire cable 47.

The solid state image sensor 41 includes a light receiving unit 41a that generates an image signal by receiving a subject image formed by the objective lenses 35a-1 to 35a-4 of the lens unit 35, and performing photoelectric conversion, and an electrode pad (not illustrated) that propagates the image signal generated by the light receiving unit 41a. A plurality of electrode pads is formed in a lower portion of the light receiving unit 41a, and a plurality of inner leads 43a extending from the FPC substrate 43 is respectively connected to the electrode pads.

The plurality of electronic components 55 to 57 forming the drive circuit of the solid state image sensor 41 is mounted on a connection land (not illustrated) of the circuit substrate 42.

The coaxial cables 46-1 and 46-2 each include a core wire 46a made of electrically-conductive material, an inner insulant 46b covering an outer periphery of the core wire 46a, a shield 46c made of electrically-conductive material that covers an outer periphery of the inner insulant 46b, and an outer insulant 46d covering an outer periphery of the shield 46c. At the distal end portion of the coaxial cables 46-1 and 46-2, the core wire 46a, the inner insulant 46b, and the shield 46c are exposed in a step-by-step manner. The single-wire cable 47 includes a core wire 47a made of electrically-conductive material, and an insulant 47b covering an outer periphery of the core wire 47a, and the core wire 47a is exposed at the distal end portion. The single-wire cable 47 is disposed between the two coaxial cables 46-1 and 46-2.

On the proximal end side of the circuit substrate 42, a step portion 42c recessed from the substrate plane on which the electronic components 55 to 57 are mounted is provided, and the exposed shields 46c of the coaxial cables 46-1 and 46-2 are electrically and mechanically connected by a solder 49b and a grand bar 48 to two shield connection electrodes 42b formed on the step portion 42c. In the first embodiment, the two shield connection electrodes 42b are provided in accordance with the number of the coaxial cables 46-1 and 46-2 to be connected. Nevertheless, one large shield connection electrode may be provided. The grand bar 48 is a plate-like metal member. In addition, in an upper portion vicinity of the step portion 42c, a first core wire connection electrode 42a-1 and a second core wire connection electrode 42a-2 are formed, and the exposed core wire 47a of the single-wire cable 47, and the exposed core wires 46a of the coaxial cables 46-1 and 46-2 are electrically and mechanically connected by a solder 49a. Here, the upper portion vicinity of the step portion 42c indicates a substrate plane that is provided in vicinity of the step portion 42c, in the substrate plane on which the electronic components 55 to 57 are mounted. As a matter of course, the step portion 42c may be provided on a substrate plane on which the electronic components 55 to 57 are not mounted, but it is desirable to provide the step portion 42c on a substrate plane on which the electronic components 55 to 57 are mounted, for making a diameter of the imaging module 100 smaller. The first core wire connection electrode 42a-1 is disposed between the two second core wire connection electrodes 42a-2, and is formed at a connectable position in a state in which the coaxial cables 46-1 and 46-2, and the single-wire cable 47 are aligned in parallel, that is, in a state in which the core wires 46a and 47a are aligned in parallel.

As illustrated in FIG. 7, the solder 49b and the grand bar 48 mechanically and electrically connect the shields 46c of the coaxial cables 46-1 and 46-2 to the shield connection electrode 42b, on the single-wire cable 47 covered by the insulant 47b, and on the shield connection electrode 42b. In this first embodiment, the single-wire cable 47 is not connected and fixed by the solder 49b, but the single-wire cable 47 may be connected and fixed by the solder 49b by increasing a supply amount of the solder 49b.

In this first embodiment, the shields 46c of the coaxial cables 46-1 and 46-2 are connected to the shield connection electrode 42b via the solder 49b and the grand bar 48, on the single-wire cable 47 covered by the insulant 47b, and on the shield connection electrode 42b. With this configuration, when stress is added to the single-wire cable 47, and the coaxial cables 46-1 and 46-2 especially in a boosting direction (direction indicated by an arrow in FIG. 6), the solder 49b and the grand bar 48 may absorb the stress, and stress to be added to the connection portion between the core wire 47a of the single-wire cable 47 and the first core wire connection electrode 42a-1 may be reduced, and disconnection of the core wire 47a, and detachment from the first core wire connection electrode 42a-1 may be prevented.

Figure 8:
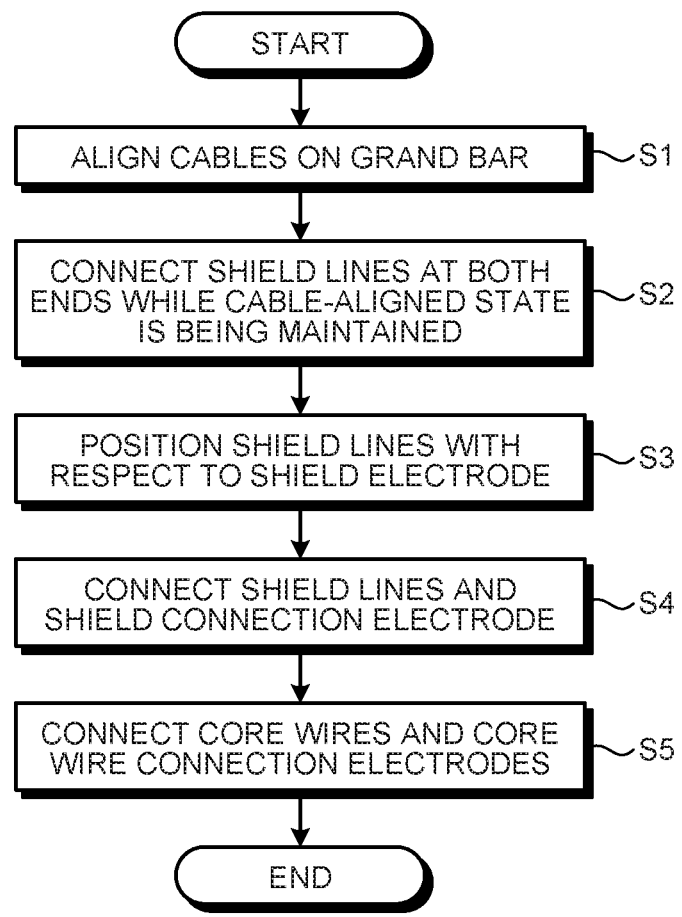
FIG. 8 is a flowchart describing a cable connection process.

Next, the connection of the single-wire cable 47, and the coaxial cables 46-1 and 46-2 to the circuit substrate 42 will be described with reference to the drawings. FIG. 8 is a flowchart describing a cable connection process.

First, the single-wire cable 47, and the coaxial cables 46-1 and 46-2 are aligned on the grand bar 48 so that the single-wire cable 47 is provided between the coaxial cables 46-1 and 46-2 (Step S1). The single-wire cable 47 covered by the insulant 47b, and the exposed shields 46c of the coaxial cables 46-1 and 46-2 are aligned so as to be positioned on the grand bar 48. In a state in which the single-wire cable 47, and the coaxial cables 46-1 and 46-2 are aligned, only the shields 46c of the coaxial cables 46-1 and 46-2 are connected by the solder 49b to the grand bar 48 (Step S2).

After the shields 46c of the coaxial cables 46-1 and 46-2 are connected to the grand bar 48, in a state in which the aligned state of the single-wire cable 47, and the coaxial cables 46-1 and 46-2 on the grand bar 48 is held by a tool or the like, they are placed on the circuit substrate 42 in an inversed state, and after the shields 46c of the coaxial cables 46-1 and 46-2 are positioned with respect to the shield connection electrode 42b (Step S3), the shields 46c are electrically and mechanically connected to the shield connection electrode 42b via solder 39b and a grand bar 48 (Step S4).

After the shields 46c are connected to the shield connection electrode 42b, the core wire 47a of the single-wire cable 47 is electrically and mechanically connected to the first core wire connection electrode 42a-1 via the solder 49a, and the core wires 46a of the coaxial cables 46-1 and 46-2 are electrically and mechanically connected to the two second core wire connection electrodes 42a-2 via the solder 49a (Step S5).

At one end, the single-wire cable 47, and the coaxial cables 46-1 and 46-2 are aligned on the grand bar 48, and the shields 46c are connected to the grand bar 48, whereby alignment fixing that is performed by the tool when the core wires 46a and shields 46c of the coaxial cables 46-1 and 46-2, and the core wire 47a of the single-wire cable 47 are connected to the shield connection electrode 42b of the circuit substrate 42, a first core wire connection electrode 42a-1, and a second core wire connection electrode 42a-2 becomes easy, and positional accuracy in alignment may be enhanced, and alignment intervals between the single-wire cable 47, and the coaxial cables 46-1 and 46-2 may be made small. With this configuration, a diameter of the imaging module 100 may be made smaller.

As described above, in the imaging module 100 according to the first embodiment, by disposing the single-wire cable 47 between the coaxial cables 46-1 and 46-2, and connecting the shields 46c to the shield connection electrode 42b via the solder 49b and the grand bar 48, on the single-wire cable 47 covered by the insulant 47b, and on a shield connection electrode 42b, stress to be added to the connection portion between the core wire 47a of the single-wire cable 47 and the first core wire connection electrode 42a-1 may be reduced, and disconnection of the core wire 47a, and detachment from the first core wire connection electrode 42a-1 may be prevented. In addition, because the single-wire cable 47, and the coaxial cables 46-1 and 46-2 are connected to the circuit substrate 42 in a state in which the shields 46c of the coaxial cables 46-1 and 46-2 are provisionally fixed via the grand bar 48, positional accuracy of the connection may be enchained, and a diameter of the imaging module 100 may be made smaller. Furthermore, because the circuit substrate 42 is provided with the step portion 42c, the shields 46c are connected to the shield connection electrode 42b on the step portion 42c, and the core wires 46a are connected to second core wire connection electrodes 42a-2 in the upper portion vicinity of the step portion 42c, connection may be performed without bending the core wires 46a, and disconnection of the core wires 46a, and detachment from the first core wire connection electrodes 42a-1 may be prevented.

First Modified Example of First Embodiment

Figure 9:
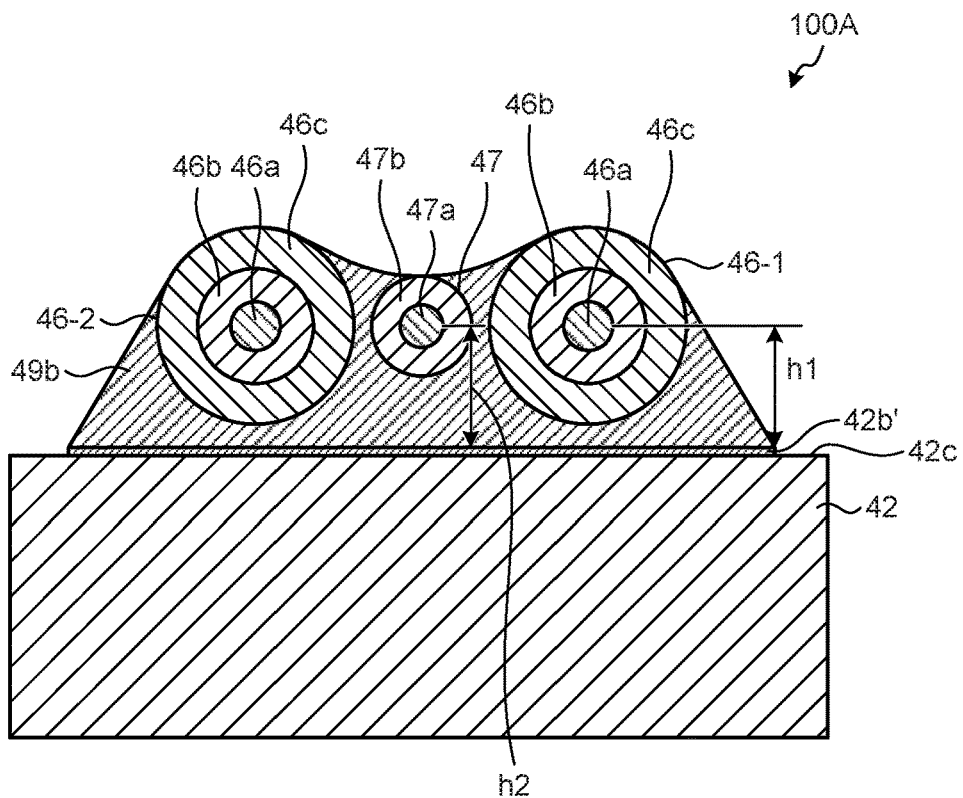
FIG. 9 is a cross-sectional view of an imaging module according to a first modified example of the first embodiment.

The connection of the shields 46c to the shield connection electrode 42b may be performed using only the solder 49b without using the grand bar 48. FIG. 9 is a cross-sectional view of an imaging module according to a first modified example of the first embodiment.

In an imaging module 100A according to the first modified example of the first embodiment, the shields 46c of the coaxial cables 46-1 and 46-2 are electrically and mechanically to one shield connection electrode 42b' only via the solder 49b. The shields 46c may be connected to the shield connection electrode 42b' without using the grand bar 48, by placing the single-wire cable 47, and the coaxial cables 46-1 and 46-2 directly on the shield connection electrode 42b' to which the solder 49b is applied, using a tool or the like, and by performing connection and fixing by melting the solder 49b.

The single-wire cable 47 is disposed between the coaxial cables 46-1 and 46-2, and the shields 46c are connected to the shield connection electrode 42b' via the solder 49b, on the single-wire cable 47 covered by the insulant 47b, and on the shield connection electrode 42b'. With this configuration, stress to be added to the connection portion between the core wire 47a of the single-wire cable 47 and the first core wire connection electrode 42a-1 may be reduced, and disconnection of the core wire 47a, and detachment from the first core wire connection electrode 42a-1 may be prevented.

In addition, in the first modified example, the single-wire cable 47 is connected and fixed by the solder 49b so that a height h1 of the core wires 46a of the coaxial cables 46-1 and 46-2 from the top of the circuit substrate 42 (from the top of the shield connection electrode 42b') on the step portion 42c on which the shield connection electrode 42b' is formed, and a height h2 of the core wire 47a of the single-wire cable 47 from the top of the circuit substrate 42 (from the top of the shield connection electrode 42b') become substantially equal. With this configuration, connection of the core wire 47a to the first core wire connection electrode 42a-1 becomes easy, and disconnection of the core wire 47a, and detachment from the first core wire connection electrode 42a-1 may be prevented more effectively.

Second Modified Example of First Embodiment

Figure 10:
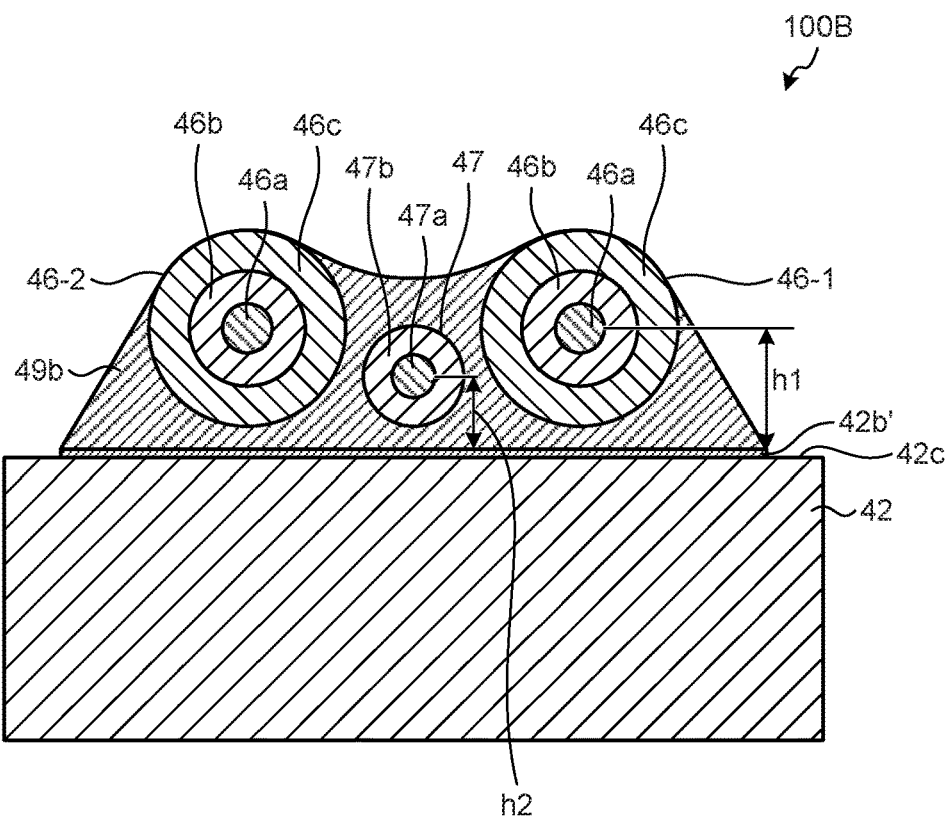
FIG. 10 is a cross-sectional view of an imaging module according to a second modified example of the first embodiment.

In the second modified example of the first embodiment, the step portion 42c is not formed on the proximal end side of the circuit substrate 42. FIG. 10 is a cross-sectional view of an imaging module according to a second modified example of the first embodiment.

In an imaging module 100B according to the second modified example of the first embodiment, a distance between the coaxial cables 46-1 and 46-2 and the shield connection electrode 42b' (distance between the shields 46c and the shield connection electrode 42b'), and a distance between the single-wire cable 47 and the shield connection electrode 42b' (distance between the insulant 47b and the shield connection electrode 42b') are substantially equal. In other words, a height h2 of the core wire 47a of the single-wire cable 47 from the top of the circuit substrate 42 is lower than a height h1 of the core wires 46a of the coaxial cables 46-1 and 46-2 from the top of the circuit substrate 42 (from the top of the step portion 42c). In the second modified example, because the step portion 42c is not formed, the core wires 46a of the coaxial cables 46-1 and 46-2 and the core wire 47a of the single-wire cable 47 need not have the same height from the circuit substrate 42. With this configuration, an interval between the coaxial cables 46-1 and 46-2 may be made smaller, and a diameter of the imaging module 100B may be made smaller.

Third Modified Example of First Embodiment

Figure 11:
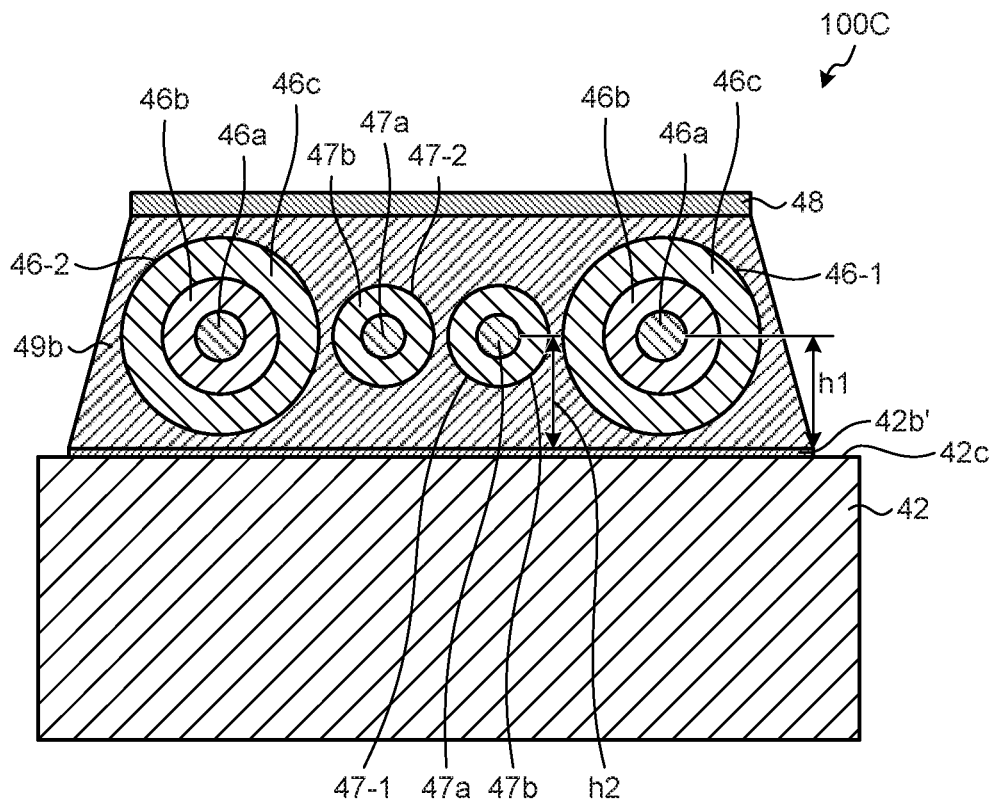
FIG. 11 is a cross-sectional view of an imaging module according to a third modified example of the first embodiment.

In the third modified example of the first embodiment, an imaging module includes two coaxial cables and two single-wire cables. FIG. 11 is a cross-sectional view of an imaging module according to a third modified example of the first embodiment.

In an imaging module 100C according to the third modified example of the first embodiment, two coaxial cables 46-1 and 46-2 and two single-wire cables 47-1 and 47-2 are connected to the circuit substrate 42. As illustrated in FIG. 11, the two single-wire cables 47-1 and 47-2 are disposed in parallel between the two coaxial cables 46-1 and 46-2. In the third modified example of the first embodiment, similarly to the first embodiment, the step portion 42c is included, and the shields 46c of the coaxial cables 46-1 and 46-2 are connected to the shield connection electrode 42b' formed on the step portion 42c, via the solder 49b and the grand bar 48, which is not illustrated in the drawing. In addition, the core wires 47a of the two single-wire cables 47-1 and 47-2 are respectively connected to the two first core wire connection electrodes 42a-1 formed in the upper portion of the step portion 42c, and the core wires 46a of the two coaxial cables 46-1 and 46-2 are respectively connected to the two second core wire connection electrodes 42a-2. Similarly to the arrangement of the single-wire cables 47-1 and 47-2 and the coaxial cables 46-1 and 46-2 in FIG. 11, the first core wire connection electrodes 42a-1 and the second core wire connection electrodes 42a-2 are disposed so that the two first core wire connection electrodes 42a-1 are positioned between the second core wire connection electrodes 42a-2.

The single-wire cables 47-1 and 47-2 are disposed between the coaxial cables 46-1 and 46-2, and the shields 46c are connected to the shield connection electrode 42b' via the solder 49b, on the single-wire cable 47 covered by the insulant 47b, and on the shield connection electrode 42b'. With this configuration, stress to be added to the connection portions between the core wires 47a of the single-wire cables 47-1 and 47-2 and the first core wire connection electrodes 42a-1 may be reduced, and disconnection of the core wires 47a, and detachment from the first core wire connection electrodes 42a-1 may be prevented.

In addition, the single-wire cables 47-1 and 47-2 are connected and fixed by the solder 49b so that a height h1 of the core wires 46a of the coaxial cables 46-1 and 46-2 from the top of the circuit substrate 42 (from the top of the shield connection electrode 42b') on the step portion 42c on which the shield connection electrode 42b' is formed, and a height h2 of the core wires 47a of the single-wire cables 47-1 and 47-2 from the top of the circuit substrate 42 (from the top of the shield connection electrode 42b') become substantially equal. With this configuration, connection of the core wire 47a to the first core wire connection electrode 42a-1 becomes easy, and disconnection of the core wire 47a, and detachment from the first core wire connection electrode 42a-1 may be prevented more effectively.

Fourth Modified Example of First Embodiment

Figure 12:
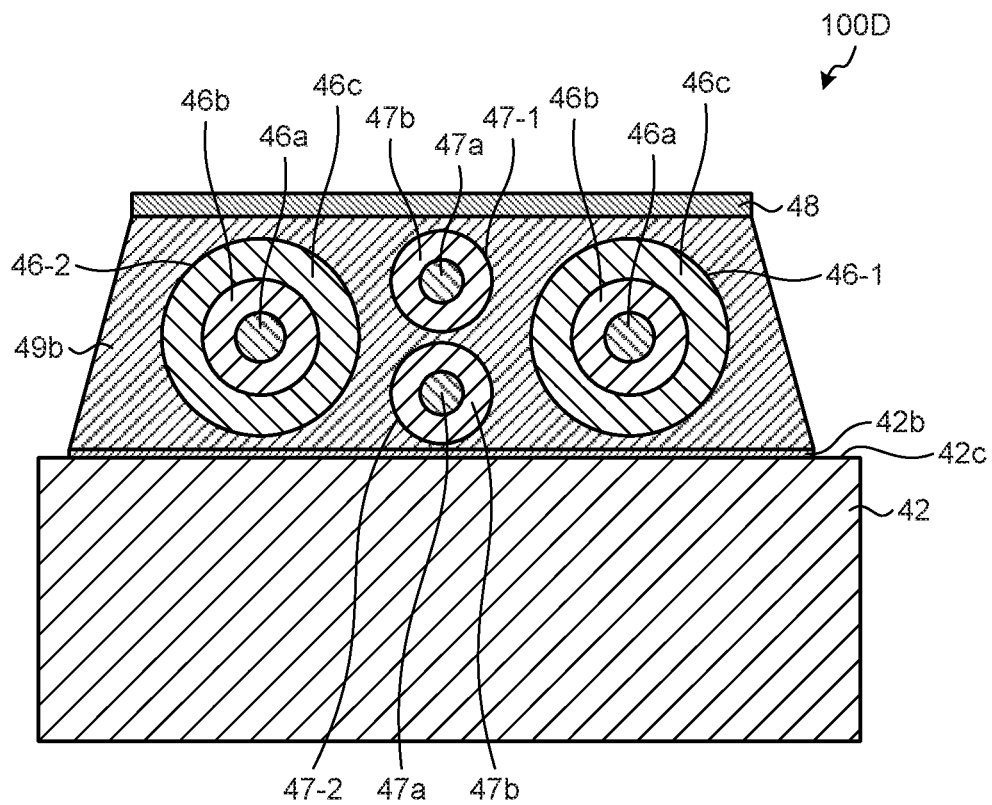
FIG. 12 is a cross-sectional view of an imaging module according to a fourth modified example of the first embodiment.

In the fourth modified example of the first embodiment, an imaging module includes two coaxial cables and two single-wire cables, and the two single-wire cables are disposed with being vertically overlapped. FIG. 12 is a cross-sectional view of an imaging module according to a fourth modified example of the first embodiment.

In an imaging module 100D according to the fourth modified example of the first embodiment, as illustrated in FIG. 12, the two single-wire cables 47-1 and 47-2 are vertically overlapped, and are disposed between the two coaxial cables 46-1 and 46-2. In the fourth modified example of the first embodiment, similarly to the first embodiment, the step portion 42c is included, and the shields 46c of the coaxial cables 46-1 and 46-2 are connected to the shield connection electrode 42b' formed on the step portion 42c, via the solder 49b and the grand bar 48, which is not illustrated in the drawing. In addition, the core wires 47a of the two single-wire cables 47-1 and 47-2 are respectively connected to the two first core wire connection electrodes 42a-1 formed in the upper portion of the step portion 42c, and the core wires 46a of the two coaxial cables 46-1 and 46-2 are respectively connected to the two second core wire connection electrodes 42a-2. The first core wire connection electrodes 42a-1 and the second core wire connection electrodes 42a-2 are disposed so that the two first core wire connection electrodes 42a-1 are positioned between the second core wire connection electrodes 42a-2.

The single-wire cables 47-1 and 47-2 are disposed between the coaxial cables 46-1 and 46-2 with being vertically overlapped, and the shields 46c are connected to the shield connection electrode 42b' via the solder 49b, on the single-wire cables 47-1 and 47-2 covered by the insulant 47b, and on the shield connection electrode 42b'. With this configuration, stress to be added to the connection portions between the core wires 47a of the single-wire cables 47-1 and 47-2 and the first core wire connection electrodes 42a-1 may be reduced, and disconnection of the core wires 47a, and detachment from the first core wire connection electrodes 42a-1 may be prevented. In addition, because the single-wire cables 47-1 and 47-2 are disposed with being vertically overlapped, an interval between the coaxial cables 46-1 and 46-2 may be made smaller, and a diameter of the imaging module 100D may be made smaller.

Fifth Modified Example of First Embodiment

Figure 13:
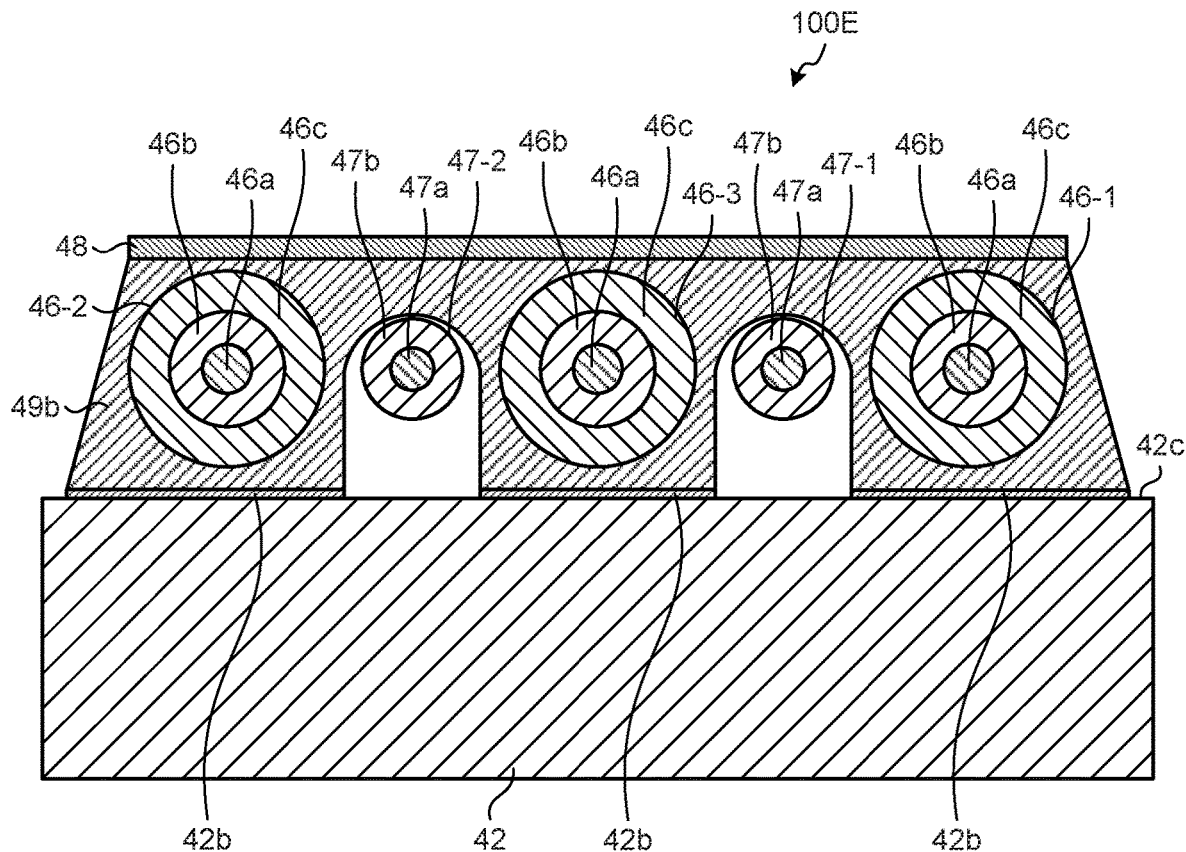
FIG. 13 is a cross-sectional view of an imaging module according to a fifth modified example of the first embodiment.

In the fifth modified example of the first embodiment, an imaging module includes three coaxial cables and two single-wire cables. FIG. 13 is a cross-sectional view of an imaging module according to a fifth modified example of the first embodiment.

In an imaging module 100E according to the fifth modified example of the first embodiment, three coaxial cables 46-1, 46-2, and 46-3, and two single-wire cables 47-1 and 47-2 are connected to the circuit substrate 42. As illustrated in FIG. 13, the two single-wire cables 47-1 and 47-2 are alternately disposed between the three coaxial cables 46-1, 46-2, and 46-3. In the fifth modified example of the first embodiment, similarly to the first embodiment, the step portion 42c is included, and the shields 46c of the coaxial cables 46-1, 46-2, and 46-3 are connected to three shield connection electrodes 42b formed on the step portion 42c, via the solder 49b and the grand bar 48, which is not illustrated in the drawing. In addition, the core wires 47a of the two single-wire cables 47-1 and 47-2 are respectively connected to the two first core wire connection electrodes 42a-1 formed in the upper portion of the step portion 42c, and the core wires 46a of the three coaxial cables 46-1, 46-2, and 46-3 are respectively connected to the three second core wire connection electrodes 42a-2. Similarly to the arrangement of the single-wire cables 47-1 and 47-2 and the coaxial cables 46-1, 46-2, and 46-3 in FIG. 13, the first core wire connection electrodes 42a-1 and the second core wire connection electrodes 42a-2 are disposed so that the two first core wire connection electrodes 42a-1 are alternately positioned between the three second core wire connection electrodes 42a-2.

The single-wire cables 47-1 and 47-2 are alternately disposed between the coaxial cables 46-1, 46-2, and 46-3, and the shields 46c are connected to the shield connection electrodes 42b via the solder 49b and the grand bar 48, on the single-wire cables 47-1 and 47-2 covered by the insulant 47b, and on the shield connection electrodes 42b. With this configuration, stress to be added to the connection portions between the core wires 47a of the single-wire cables 47-1 and 47-2 and the first core wire connection electrodes 42a-1 may be reduced, and disconnection of the core wires 47a, and detachment from the first core wire connection electrodes 42a-1 may be prevented. In addition, in this fifth modified example, the two single-wire cables 47-1 and 47-2 are alternately disposed between the three coaxial cables 46-1, 46-2, and 46-3, but it is enough that the two single-wire cables 47-1 and 47-2 are disposed between any two of the three coaxial cables 46-1, 46-2, and 46-3.

Sixth Modified Example of First Embodiment

Figure 14:
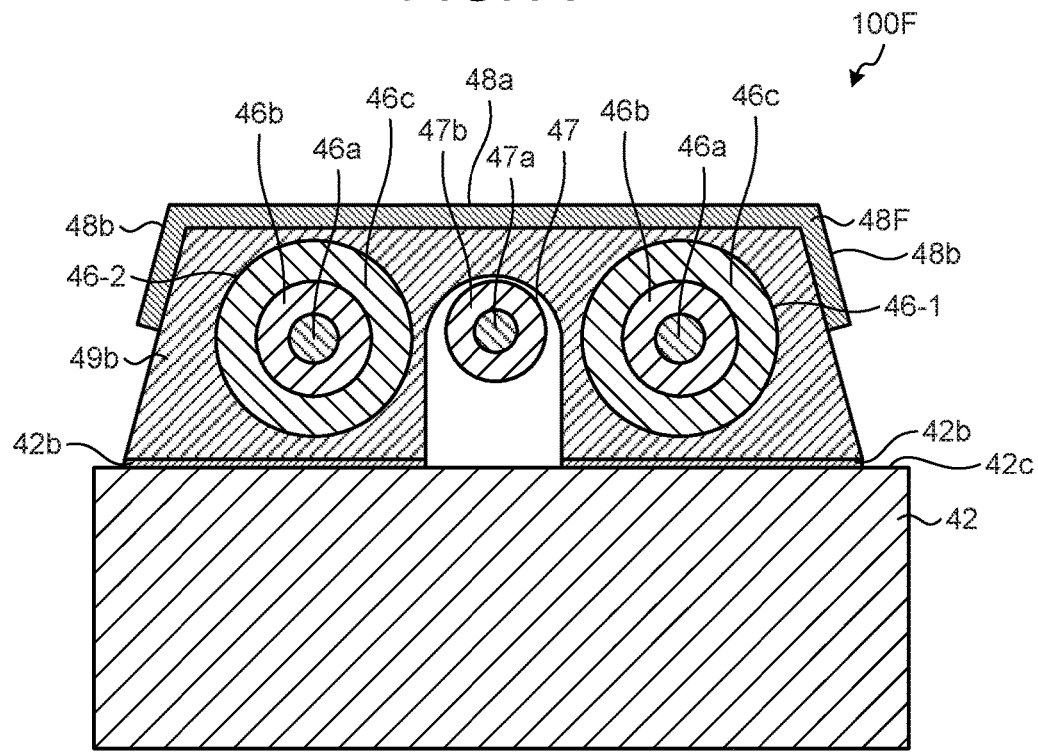
FIG. 14 is a cross-sectional view of an imaging module according to a sixth modified example of the first embodiment.

In the sixth modified example of the first embodiment, a grand bar includes a plate-like main body portion, and wall portions rising up from the main body portion. FIG. 14 is a cross-sectional view of an imaging module according to a sixth modified example of the first embodiment.

In an imaging module 100F according to the sixth modified example of the first embodiment, two coaxial cables 46-1 and 46-2 and one single-wire cable 47 are connected to the circuit substrate 42. As illustrated in FIG. 14, a grand bar 48F that prevents disconnection of the core wire 47a of the single-wire cable 47, and detachment from the first core wire connection electrode 42a-1, together with the solder 49b, includes a plate-like main body portion 48a, and wall portions 48b rising up from the main body portion 48a. When the single-wire cable 47, and the coaxial cables 46-1 and 46-2 are aligned on the grand bar 48F, the alignment is facilitated by the wall portions 48b. In addition, in the sixth modified example of the first embodiment, similarly to the first embodiment, the step portion 42c is included, and the shields 46c of the coaxial cables 46-1 and 46-2 are connected to the shield connection electrodes 42b formed on the step portion 42c, via the solder 49b and the grand bar 48F, and the core wire 47a of the single-wire cable 47 is connected to the one first core wire connection electrode 42a-1 formed in the upper portion vicinity of the step portion 42c, and the core wires 46a of the two coaxial cables 46-1 and 46-2 are respectively connected to the two second core wire connection electrodes 42a-2.

In addition, in the sixth modified example, because the single-wire cable 47 is disposed between the coaxial cables 46-1 and 46-2, and the shields 46c are connected to the shield connection electrodes 42b via the solder 49b and the grand bar 48F, on the single-wire cable 47 covered by the insulant 47b, and on the shield connection electrodes 42b, stress to be added to the connection portion between the core wire 47a of the single-wire cable 47 and the first core wire connection electrode 42a-1 may be reduced, and disconnection of the core wire 47a, and detachment from the first core wire connection electrode 42a-1 may be prevented.

Seventh Modified Example of First Embodiment

Figure 15:
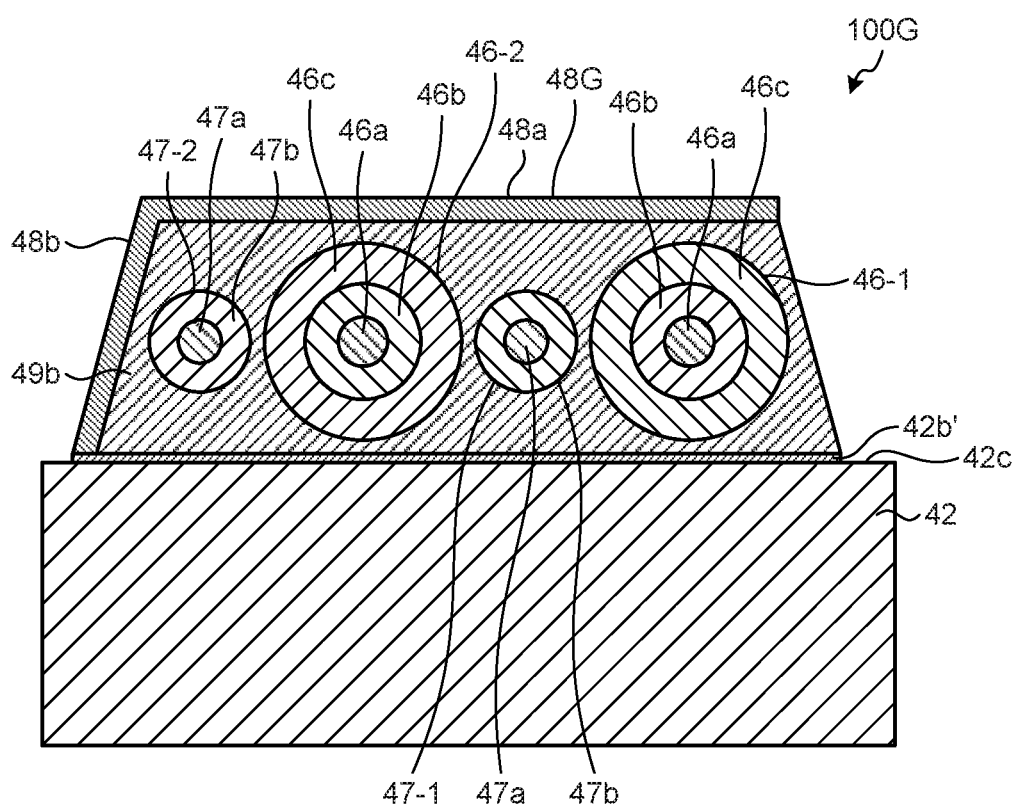
FIG. 15 is a cross-sectional view of an imaging module according to a seventh modified example of the first embodiment.

In the seventh modified example of the first embodiment, an imaging module includes two coaxial cables and two single-wire cables, and a grand bar includes a plate-like main body portion, and a wall portion rising up from the main body portion. FIG. 15 is a cross-sectional view of an imaging module according to a seventh modified example of the first embodiment.

In an imaging module 100G according to the seventh modified example of the first embodiment, two coaxial cables 46-1 and 46-2 and two single-wire cables 47-1 and 47-2 are alternately connected to the circuit substrate 42. As illustrated in FIG. 15, a grand bar 48G includes a plate-like main body portion 48a, and a wall portion 48b rising up from the main body portion 48a. The wall portion 48b is provided on only one side of the main body portion 48a. The single-wire cable 47-1 is disposed between the coaxial cables 46-1 and 46-2, and the single-wire cable 47-2 is disposed between the coaxial cable 46-2 and the wall portion 48b of the grand bar 48G. In addition, in the seventh modified example of the first embodiment, similarly to the first embodiment, the step portion 42c is included, and the shields 46c of the coaxial cables 46-1 and 46-2 are connected to the shield connection electrode 42b' formed on the step portion 42c, via the solder 49b and the grand bar 48G, and the core wires 47a of the two single-wire cables 47-1 and 47-2 are respectively connected to the two first core wire connection electrodes 42a-1 formed in the upper portion vicinity of the step portion 42c, and the core wires 46a of the two coaxial cables 46-1 and 46-2 are respectively connected to the two second core wire connection electrodes 42a-2. The first core wire connection electrodes 42a-1 and the second core wire connection electrodes 42a-2 are alternately disposed similarly to the single-wire cables 47-1 and 47-2 and the coaxial cables 46-1 and 46-2 in FIG. 15.

In the seventh modified example, because the single-wire cables 47-1 and 47-2 are disposed between the coaxial cables 46-1 and 46-2, or between a coaxial cable 46-2 and the wall portion 48b of the grand bar 48G, and the shields 46c are connected to the shield connection electrode 42b' via the solder 49b and the grand bar 48G, on the single-wire cables 47-1 and 47-2 covered by the insulant 47b, and on the shield connection electrode 42b', stress to be added to the connection portions between the core wires 47a of the single-wire cables 47-1 and 47-2 and the first core wire connection electrodes 42a-1 may be reduced, and disconnection of the core wires 47a, and detachment from the first core wire connection electrodes 42a-1 may be prevented. In addition, when the single-wire cables 47-1 and 47-2 and the coaxial cables 46-1 and 46-2 are aligned on the grand bar 48G, the alignment is facilitated by the wall portion 48b.

Second Embodiment

Figure 16:
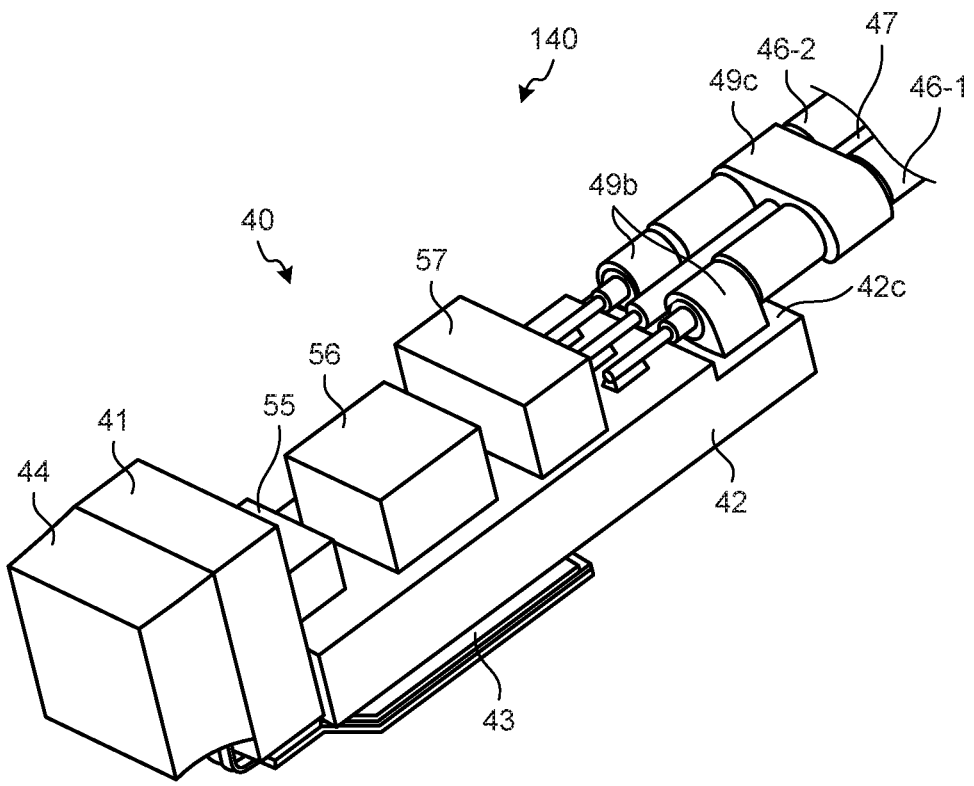
FIG. 16 is a perspective view of an imaging module according to a second embodiment.
Figure 17:
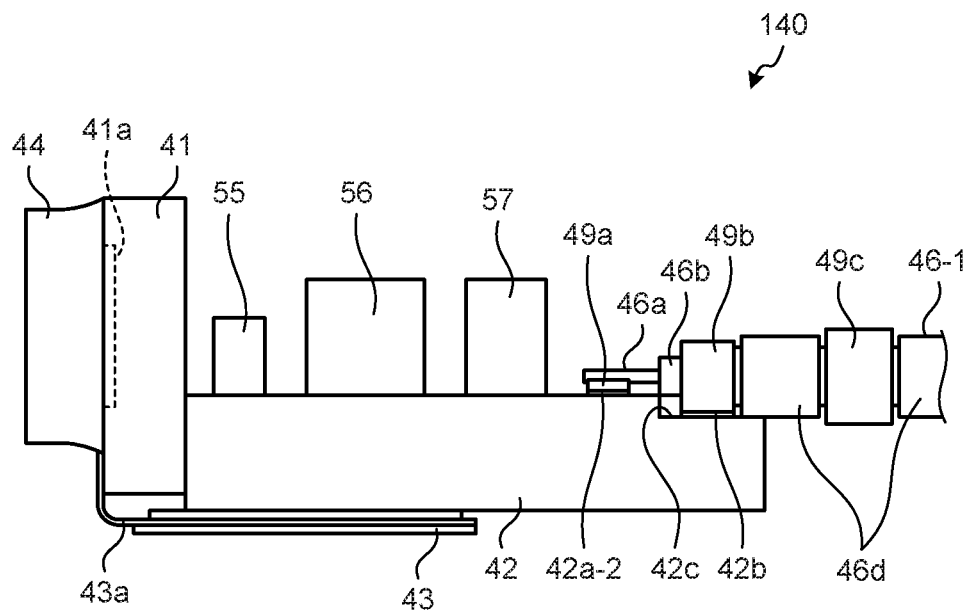
FIG. 17 is a side view of the imaging module according to the second embodiment.
Figure 18:
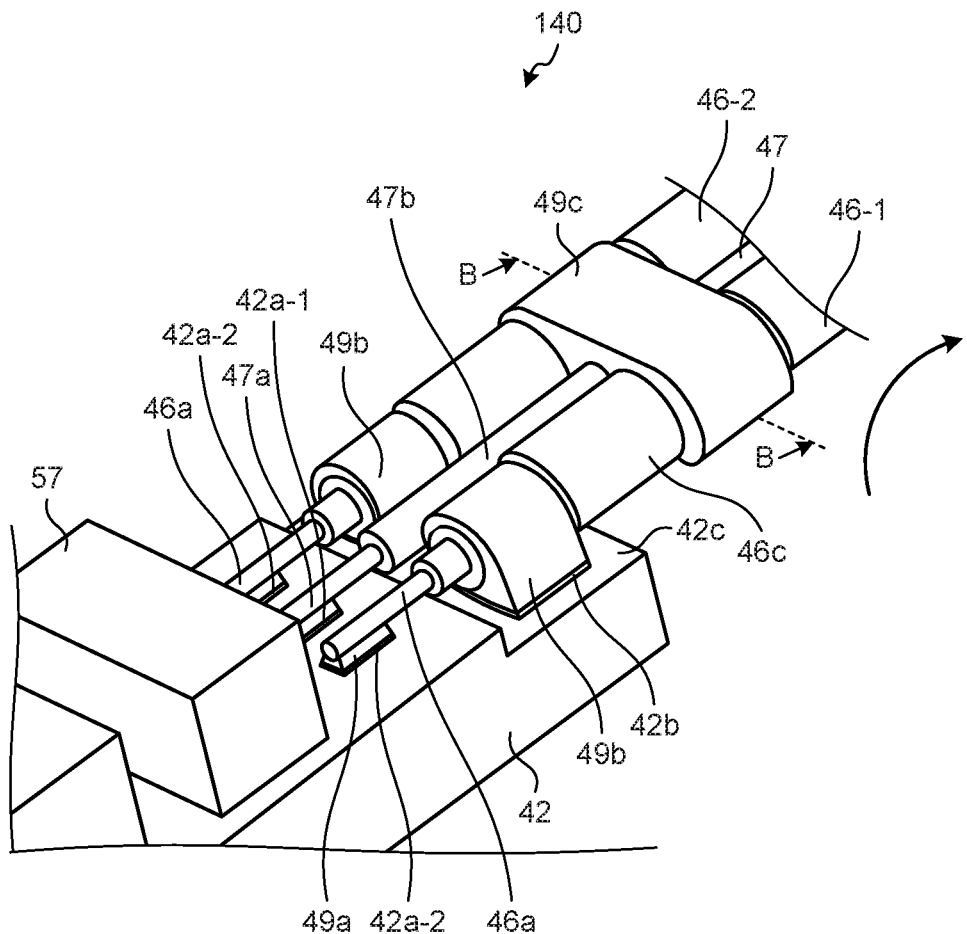
FIG. 18 is a partially-enlarged perspective view of the imaging module according to the second embodiment.
Figure 19:
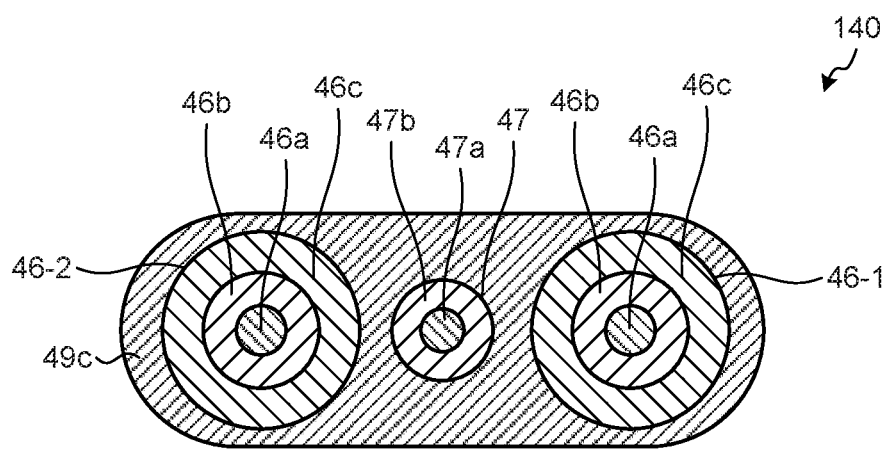
FIG. 19 is a B-B line cross-sectional view of the imaging module illustrated in FIG. 18.

In the second embodiment, a shield is connected by a solder on a shield connection electrode, and furthermore, the shield is connected also on a proximal end side of a coaxial cable of the shield connection electrode. FIG. 16 is a perspective view of an imaging module according to the second embodiment. FIG. 17 is a side view of the imaging module according to the second embodiment. FIG. 18 is a partially-enlarged perspective view of the imaging module according to the second embodiment. FIG. 19 is a B-B line cross-sectional view of the imaging module illustrated in FIG. 18.

In an imaging module 140 according to the second embodiment, one single-wire cable 47 and two coaxial cables 46-1 and 46-2 are connected to the circuit substrate 42. Two shield connection electrodes 42b are formed on the step portion 42c of the circuit substrate 42, and the shields 46c of the coaxial cables 46-1 and 46-2 are electrically and mechanically to the respective shield connection electrodes 42b by the solder 49b. In the second embodiment, the solder 49b that connects the shield connection electrodes 42b and the shields 46c does not exist on the single-wire cable 47, and does not connect and fix the single-wire cable 47, but the single-wire cable 47 may be connected and fixed by the solder 49b via the insulant 47b.

In the coaxial cables 46-1 and 46-2, the core wires 46a, the inner insulants 46b, and the shields 46c are exposed in a step-by-step manner, but on the proximal end side of a position at which the exposed shields 46c are connected to the shield connection electrodes 42b by the solder 49b, the outer insulants 46d are further removed, and the shields 46c are exposed. In the second embodiment, the exposed portions of the shields 46c are connected by a solder 49c. When connecting the shields 46c, the solder 49c simultaneously connects and fixes the single-wire cable 47 disposed between the coaxial cables 46-1 and 46-2. With this configuration, stress to be added to the connection portion between the core wire 47a of the single-wire cable 47 and the first core wire connection electrode 42a-1 may be reduced, and disconnection of the core wire 47a, and detachment from the first core wire connection electrode 42a-1 may be prevented. In addition, a plate-like solder may be used as the solder 49c, and adhesion and fixing may be performed by heating and melting the solder 49c after the alignment is performed by surrounding the exposed portions of the shields 46c of the coaxial cables 46-1 and 46-2 and the periphery of the single-wire cable 47 using the solder 49c.

Additional Statement 1

In a cable connection structure in which at least one single-wire cable and at least one coaxial cable are respectively connected to electrodes provided on a substrate, the single-wire cable includes a core wire made of electrically-conductive material, and an insulant covering an outer periphery of the core wire, and the core wire is exposed at a distal end portion, to be connected to a first core wire connection electrode of the substrate, the coaxial cable includes a core wire made of electrically-conductive material, an inner insulant covering an outer periphery of the core wire, a shield made of electrically-conductive material that covers an outer periphery of the inner insulant, and an outer insulant covering an outer periphery of the shield, and the core wire, the inner insulant, and the shield are exposed in a step-by-step manner at a distal end portion, and the core wire and the shield are respectively connected to a second core wire connection electrode and a shield connection electrode of the substrate, the single-wire cable is disposed to be positioned between the coaxial cable and a conductive member, and an exposed shield of the coaxial cable is connected by the conductive member, and the conductive member connects the shield on the single-wire cable covered by the insulant, and on the shield connection electrode, and/or on a proximal end side of the shield connection electrode.

By connecting shields of two coaxial cables using a conductive member, on a single-wire cable covered by an insulant, and on a shield connection electrode, and/or on a proximal end side of the shield connection electrode, the present disclosure may suppress transmission of stress to a core wire of the single-wire cable, by the connection of the shields that is caused by the conductive member, when the stress is added in a direction of going away from the substrate, and may prevent disconnection of the core wire and detachment from a connected location.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection structure comprising:
   a substrate including a first core wire connection electrode, at least two second core wire connection electrodes, and one or more shield connection electrodes;
   a single-wire cable comprising:
      a first core wire made of electrically-conductive material, and
      an insulant covering an outer periphery of the first core wire,
      wherein the first core wire is exposed at a distal end portion, and connected to the first core wire connection electrode;
   at least two coaxial cables each comprising:
      a second core wire made of electrically-conductive material,
      an inner insulant covering an outer periphery of the second core wire,
      a shield made of electrically-conductive material that covers an outer periphery of the inner insulant, and
      an outer insulant covering an outer periphery of the shield,
      wherein the second core wire, the inner insulant, and the shield are exposed in a step-by-step manner at a distal end portion of each of the at least two coaxial cables, the second core wire of each of the at least two coaxial cables is connected to a respective one of the at least two second core wire connection electrodes and the shield of each of the at least two coaxial cables is connected to the one or more shield connection electrodes; and a conductive member connecting exposed portions of the shield of each of the at least two coaxial cables, wherein the first core wire connection electrode of the single-wire cable is disposed between the at least two second core wire connection electrodes of the at least two coaxial cables, the conductive member is disposed directly on an upper surface of the insulant covering the single-wire cable, and the conductive member connects the shield of each of the at least two coaxial cables on at least one of a position on the one or more shield connection electrodes and a position closer to a proximal end side than the position on the at least one shield connection electrodes.

2. The cable connection structure according to claim 1, wherein the substrate includes a step formed on a surface of the substrate on a side to which the single-wire cable and the at least two coaxial cables are connected, the step dividing the surface of the substrate into a lower surface and an upper surface, the one or more shield connection is electrodes being formed on the lower surface, and the first core wire connection electrode and the at least two second core wire connection electrodes being formed on the upper surface.

3. The cable connection structure according to claim 1, wherein the conductive member is a solder used for connection of the shield of each of the at least two coaxial cables and the one or more shield connection electrodes.

4. The cable connection structure according to claim 1, wherein the conductive member comprises a solder and a plate-like metal member that are used for connection of the shield of each of the at least two coaxial cables and the one or more shield connection electrodes.

5. The cable connection structure according to claim 2, wherein the conductive member is configured to fix the at least two coaxial cables and the single-wire cable such that a first height of the second core wire of each of the at least two coaxial cables from the lower surface is substantially equal to a second height of the first core wire of the single-wire cable from the lower surface.

6. An imaging module comprising:
the cable connection structure according to claim 1;
an image sensor connected to an external electrode formed on the substrate of the cable connection structure, the image sensor being configured to convert light that has entered from outside, into an electrical signal; and
an optical system configured to collect light and cause the collected light to enter the image sensor.

7. An endoscope comprising:
an insertion portion including a distal end portion having a cylindrical shape formed of a rigid member, the insertion portion being configured to be inserted into a subject; and
the imaging module according to claim 6 disposed in the rigid member.

8. The cable connection structure according to claim 1, wherein an outer diameter of the insulant of the single-wire cable is smaller than an outer diameter of the outer insulant of each of the at least two coaxial cables.

* * * * *